(12) United States Patent
Shifflette et al.

(10) Patent No.: US 9,572,928 B2
(45) Date of Patent: Feb. 21, 2017

(54) SUBSTANCE DELIVERY DEVICES, SYSTEMS AND METHODS

(71) Applicant: MRI Interventions, Inc., Memphis, TN (US)

(72) Inventors: J. Michael Shifflette, Alachua, FL (US); Peter Piferi, Orange, CA (US)

(73) Assignee: MRI Interventions, Inc., Irvine, CA (US)

( * ) Notice: Subject to any disclaimer, the term of this patent is extended or adjusted under 35 U.S.C. 154(b) by 185 days.

(21) Appl. No.: 14/204,378

(22) Filed: Mar. 11, 2014

(65) Prior Publication Data

US 2014/0276582 A1    Sep. 18, 2014

Related U.S. Application Data

(60) Provisional application No. 61/779,395, filed on Mar. 13, 2013.

(51) Int. Cl.
| | |
|---|---|
| *A61M 37/00* | (2006.01) |
| *A61M 5/145* | (2006.01) |
| *A61M 25/02* | (2006.01) |

(52) U.S. Cl.
CPC .......... *A61M 5/14593* (2013.01); *A61B 90/11* (2016.02); *A61M 5/14526* (2013.01); *A61M 25/02* (2013.01); *A61M 2005/14513* (2013.01)

(58) Field of Classification Search
CPC ............... A61M 2005/14513; A61M 5/14593; A61M 5/14526; A61B 90/11
See application file for complete search history.

(56) References Cited

U.S. PATENT DOCUMENTS

| | | | |
|---|---|---|---|
| 6,026,316 A | 2/2000 | Kucharczyk et al. | |
| 6,050,992 A | 4/2000 | Nichols | |
| 6,167,311 A | 12/2000 | Rezai | |
| 6,356,786 B1 | 3/2002 | Rezai et al. | |
| 6,405,079 B1 | 6/2002 | Ansarinia | |
| 6,438,423 B1 | 8/2002 | Rezai et al. | |
| 6,526,318 B1 | 2/2003 | Ansarinia | |
| 6,539,263 B1 | 3/2003 | Schiff et al. | |
| 6,609,030 B1 | 8/2003 | Rezai et al. | |
| 6,708,064 B2 | 3/2004 | Rezai | |
| 8,374,677 B2 | 2/2013 | Piferi et al. | |
| 2005/0119618 A1* | 6/2005 | Gonnelli | A61M 5/1452 604/150 |
| 2007/0148014 A1* | 6/2007 | Anex | A61M 5/14526 417/392 |
| 2008/0086111 A1* | 4/2008 | Cowan | A61M 5/14216 604/522 |

(Continued)

*Primary Examiner* — Emily Schmidt
(74) *Attorney, Agent, or Firm* — Myers Bigel, P.A.

(57) ABSTRACT

A substance delivery device includes an elongated tubular body having opposing proximal and distal ends, and a diaphragm that is in slideable sealing engagement with an inside wall of the tubular body. The diaphragm is movable in opposite first and second directions within the tubular body. A substance is contained within the tubular body between the diaphragm and the tubular body distal end, and a slave fluid is contained within the tubular body between the diaphragm and the tubular body proximal end. When pressure is exerted on the slave fluid, the slave fluid causes the diaphragm to move and eject the substance through the tubular body distal end.

13 Claims, 10 Drawing Sheets

(56) References Cited

U.S. PATENT DOCUMENTS

| | | | |
|---|---|---|---|
| 2010/0305507 A1* | 12/2010 | Duncan | A61M 5/14526 604/121 |
| 2012/0191102 A1* | 7/2012 | Matsumoto | A61B 17/8822 606/94 |
| 2013/0030408 A1 | 1/2013 | Piferi et al. | |

\* cited by examiner

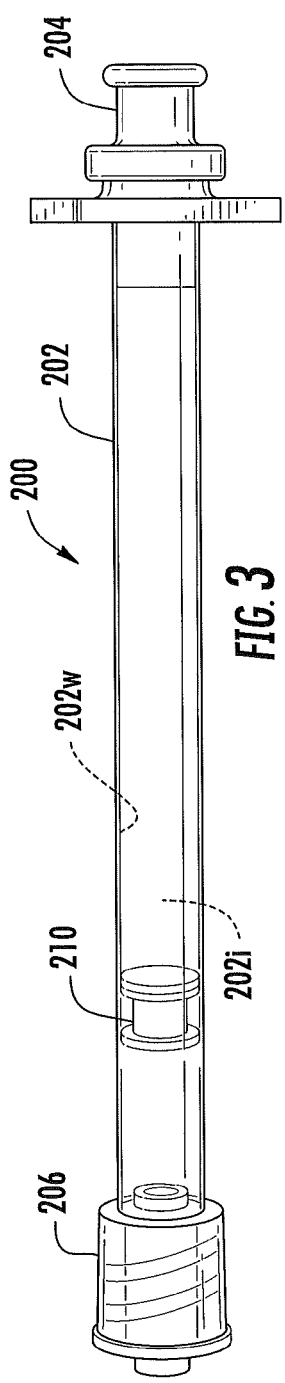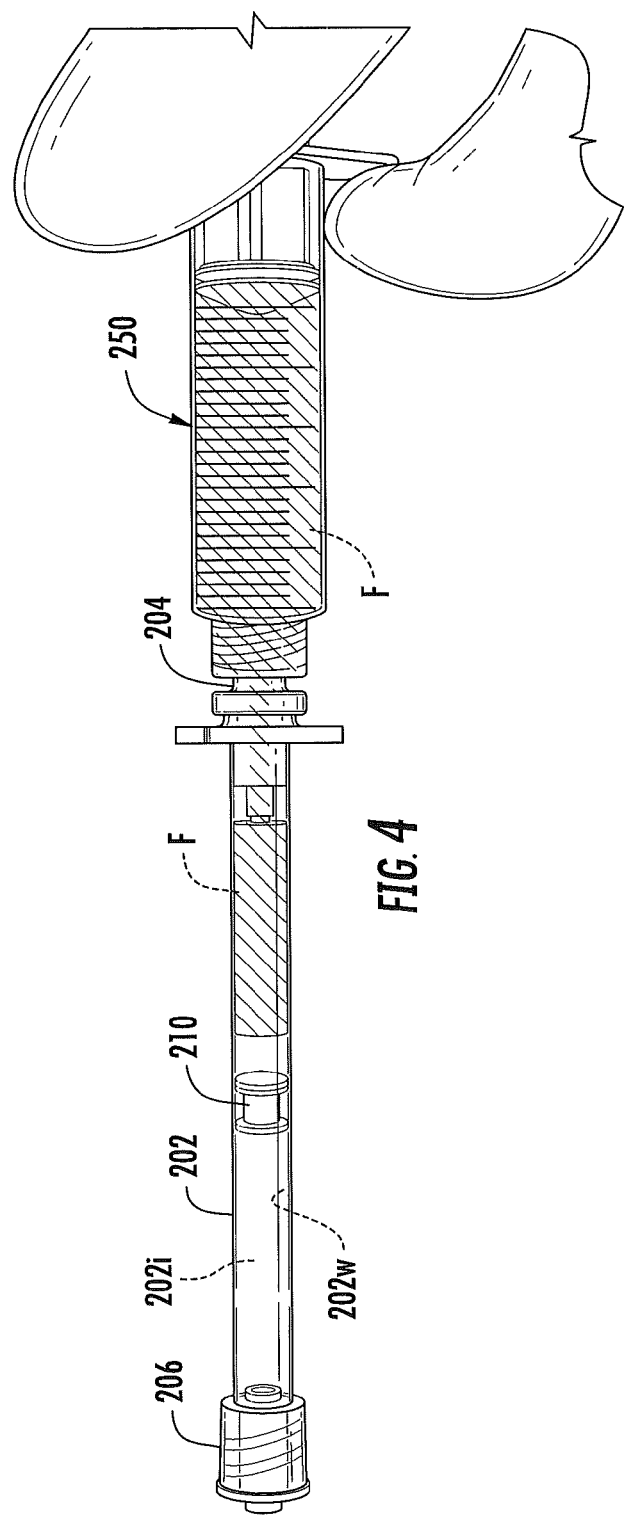
FIG. 3
FIG. 4

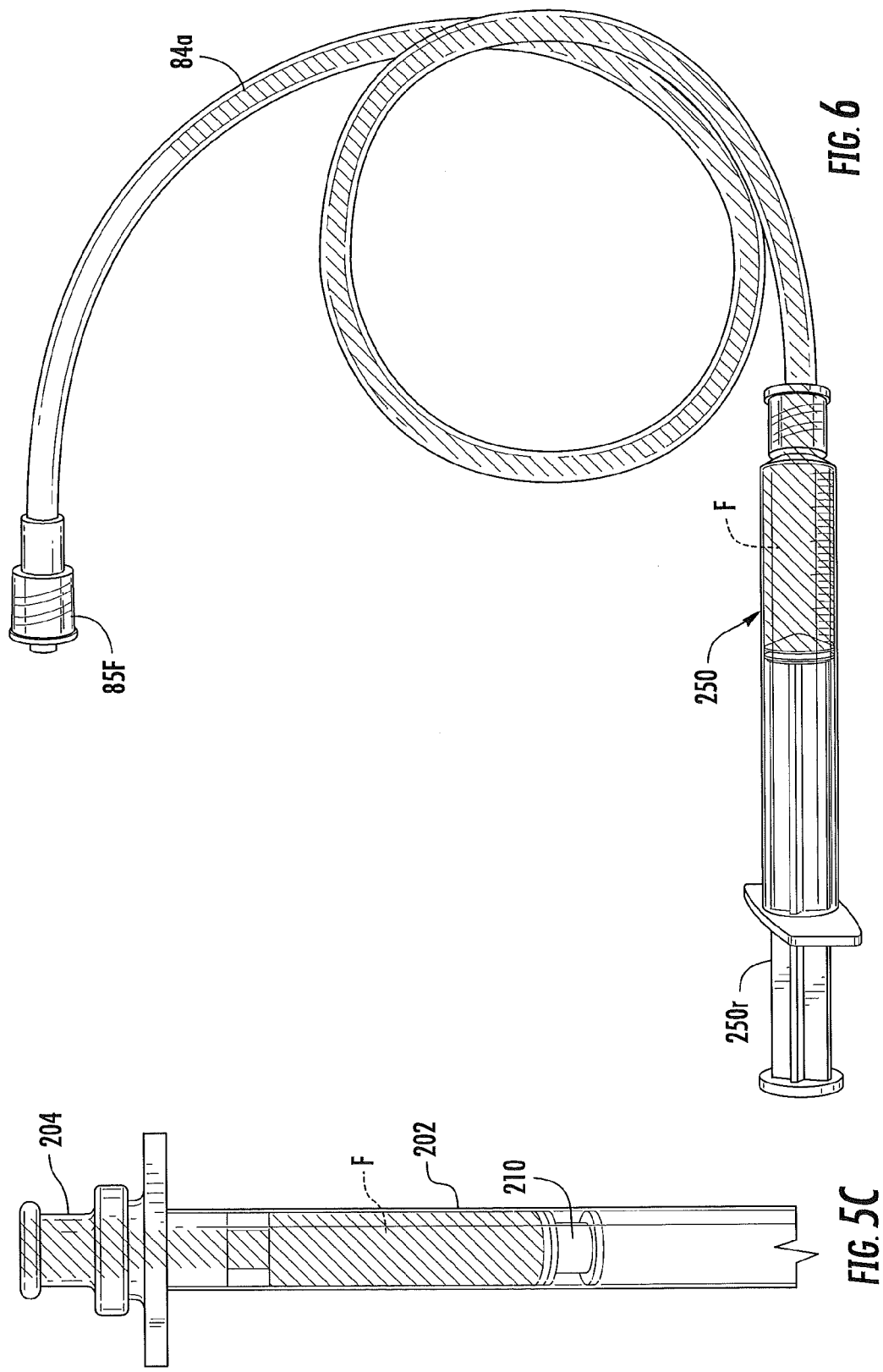

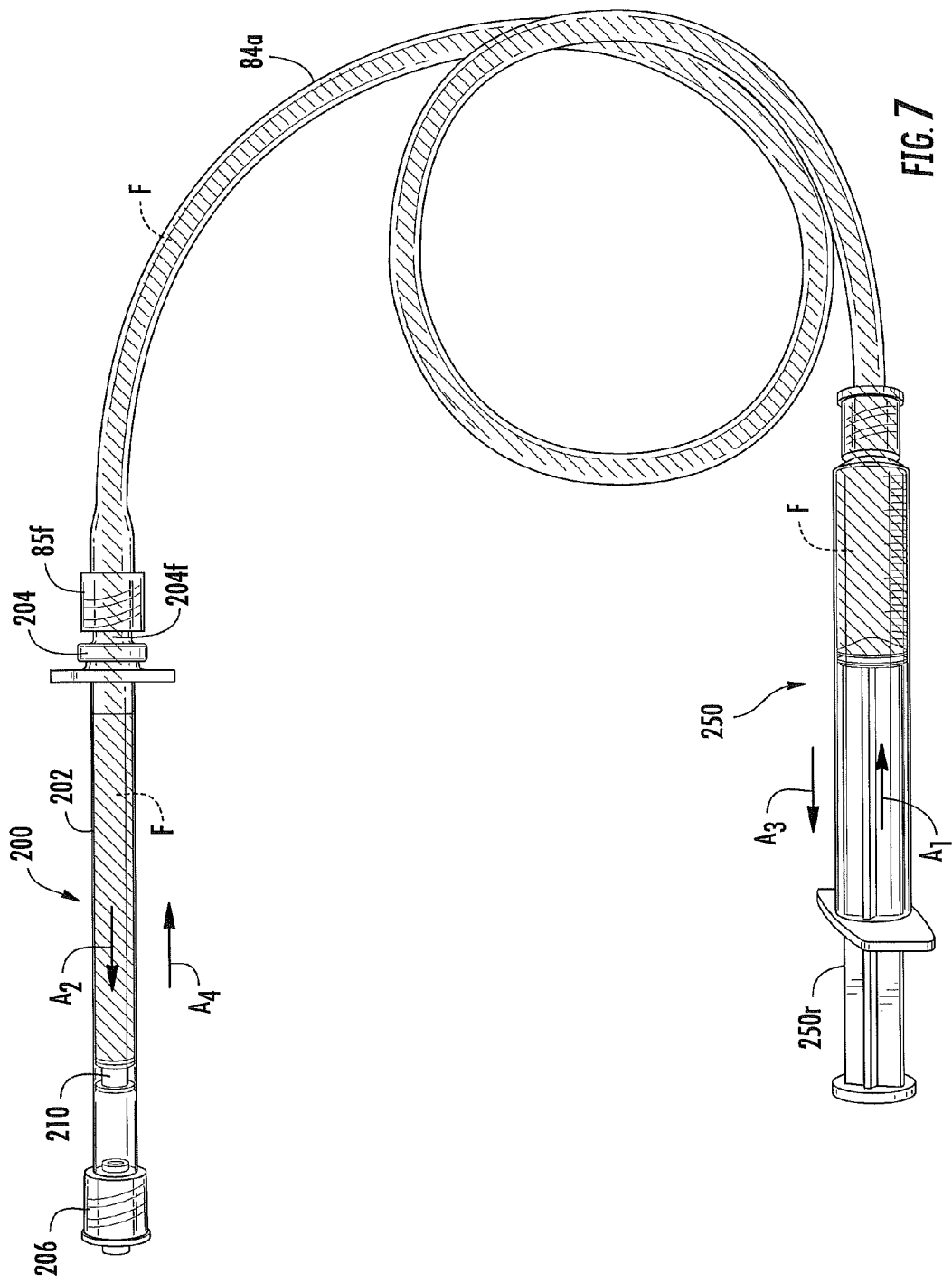

SUBSTANCE DELIVERY DEVICES, SYSTEMS AND METHODS

RELATED APPLICATION

This application claims the benefit of and priority to U.S. Provisional Patent Application No. 61/779,395 filed Mar. 13, 2013, the disclosure of which is incorporated herein by reference as if set forth in its entirety.

FIELD OF THE INVENTION

The present invention relates generally to medical devices and systems and, more particularly, to devices and systems for delivering substances in vivo, and may be particularly suitable for MRI-guided procedures.

BACKGROUND

Various therapeutic and diagnostic procedures require that a substance be infused into a prescribed region of a patient, such as into a target deep brain location in the patient's brain, using a delivery cannula. It may be important or critical that the substance be delivered with high accuracy to the target region in the patient and without undue trauma to the patient. MRI-guided deliveries typically employ long lengths of tubing resulting in relatively large "dead spaces" that often result in a volume of medical substance that may be wasted or unused. Because of the high cost of such medical substances, it may be desirable to reduce the amount of substance that is wasted or unused.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a substance delivery device includes an elongated tubular body having opposing proximal and distal ends, and a diaphragm that is in slideable sealing engagement with an inside wall of the tubular body. The diaphragm is movable in opposite first and second directions within the tubular body. A substance is contained within the tubular body between the diaphragm and the tubular body distal end, and a slave fluid is contained within the tubular body between the diaphragm and the tubular body proximal end. Typically, a volume of the substance contained within the tubular body is less than a volume of the slave fluid contained within the tubular body. When pressure is exerted on the slave fluid, for example via a syringe, the slave fluid causes the diaphragm to move and eject the substance through the tubular body distal end.

In some embodiments, the tubular body and diaphragm comprise MRI-compatible material.

In some embodiments, the tubular body proximal and distal ends are adapted to removably receive tubing and such that the tubing is in fluid communication with the tubular body.

According to some embodiments of the present invention, a system for delivering a substance to a patient includes a substance delivery device that contains the substance, and a syringe in fluid communication with the substance delivery device for ejecting the substance from the substance delivery device. The substance delivery device includes an elongated tubular body having opposing proximal and distal ends. A diaphragm is in slideable sealing engagement with an inside wall of the tubular body, and is movable in opposite first and second directions within the tubular body. In some embodiments, the tubular body and diaphragm are MRI-compatible.

The substance is contained within the tubular body between the diaphragm and the tubular body distal end. The syringe is in fluid communication with the tubular body proximal end and contains a slave fluid. User activation of the syringe causes the slave fluid to move the diaphragm in the first direction which, in turn, causes the substance to be ejected through the tubular body distal end. User activation of the syringe also causes the slave fluid to move the diaphragm in the second direction which, in turn, causes the substance to be drawn into the tubular body through the distal end thereof.

In some embodiments, the system includes a cannula that is in fluid communication with the tubular body distal end, typically via tubing connected to the tubular body distal end. The cannula is adapted to transfer the substance to a selected region in a patient. In some embodiments, the cannula is MRI-compatible.

In some embodiments, the system includes a pump adapted to activate the syringe and to cause the slave fluid to move the diaphragm such that the substance is forced out of the tubular body distal end.

According to some embodiments of the present invention, a method for delivering a substance to a patient, for example in an MRI-guided surgical procedure, includes inserting a cannula into a selected region of the patient, wherein the cannula comprises a lumen that is in fluid communication with a substance delivery device containing the substance, and transferring the substance from the substance delivery device to the selected region through the lumen via a slave fluid. In some embodiments, the substance delivery device includes an elongated tubular body having opposing proximal and distal ends, and a diaphragm in slideable sealing engagement with an inside wall of the tubular body. The step of transferring the substance includes moving the diaphragm via the slave fluid.

According other embodiments of the present invention, a method of preparing a substance delivery device for use in delivering a substance to a patient, for example in an MRI-guided surgical procedure, is disclosed. The substance delivery device includes an elongated tubular body having opposing proximal and distal ends, and a diaphragm in slideable sealing engagement with an inside wall of the tubular body. The method includes loading a slave fluid into the substance delivery device via the proximal end, and then loading the substance into the substance delivery device via the distal end by pulling the diaphragm towards the tubular body proximal end via the slave fluid. Trapped air is removed from the slave fluid after loading the slave fluid into the substance delivery device, and trapped air is removed from the substance after loading the substance into the substance delivery device.

According other embodiments of the present invention, a drug delivery device includes an MRI-compatible elongated tubular body comprising a liquid medicament (e.g., a brain therapy medicament, etc.) in a first volume and a slave fluid in a second volume separated by a diaphragm in slideable sealing engagement with an inside wall of the tubular body. The first volume is less than the second volume. In some embodiments, the first volume is less than twenty microliters (20 µL). In some embodiments, the first volume is between about twenty microliters (20 µL) and about thirty milliliters (30 cc). In some embodiments, the tubular body includes opposite proximal and distal ends having respective connectors configured to releasably engage tubing.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIG. 3 is a perspective view of a substance delivery device, according to some embodiments of the present invention.

FIGS. 4 and 5A-5C illustrate exemplary operations for loading a slave fluid into the substance delivery device of FIG. 3.

FIG. 6 is a perspective view of a syringe containing a slave fluid and tubing connected to the syringe that is being filled with the slave fluid.

FIG. 7 is a perspective view of the syringe and tubing of FIG. 6 connected to a proximal end of the tubular body portion of the substance delivery device of FIG. 5C. The slave fluid between the syringe plunger and the diaphragm in the tubular body of the substance delivery device is substantially or totally free of trapped air.

DETAILED DESCRIPTION

Figure 1:
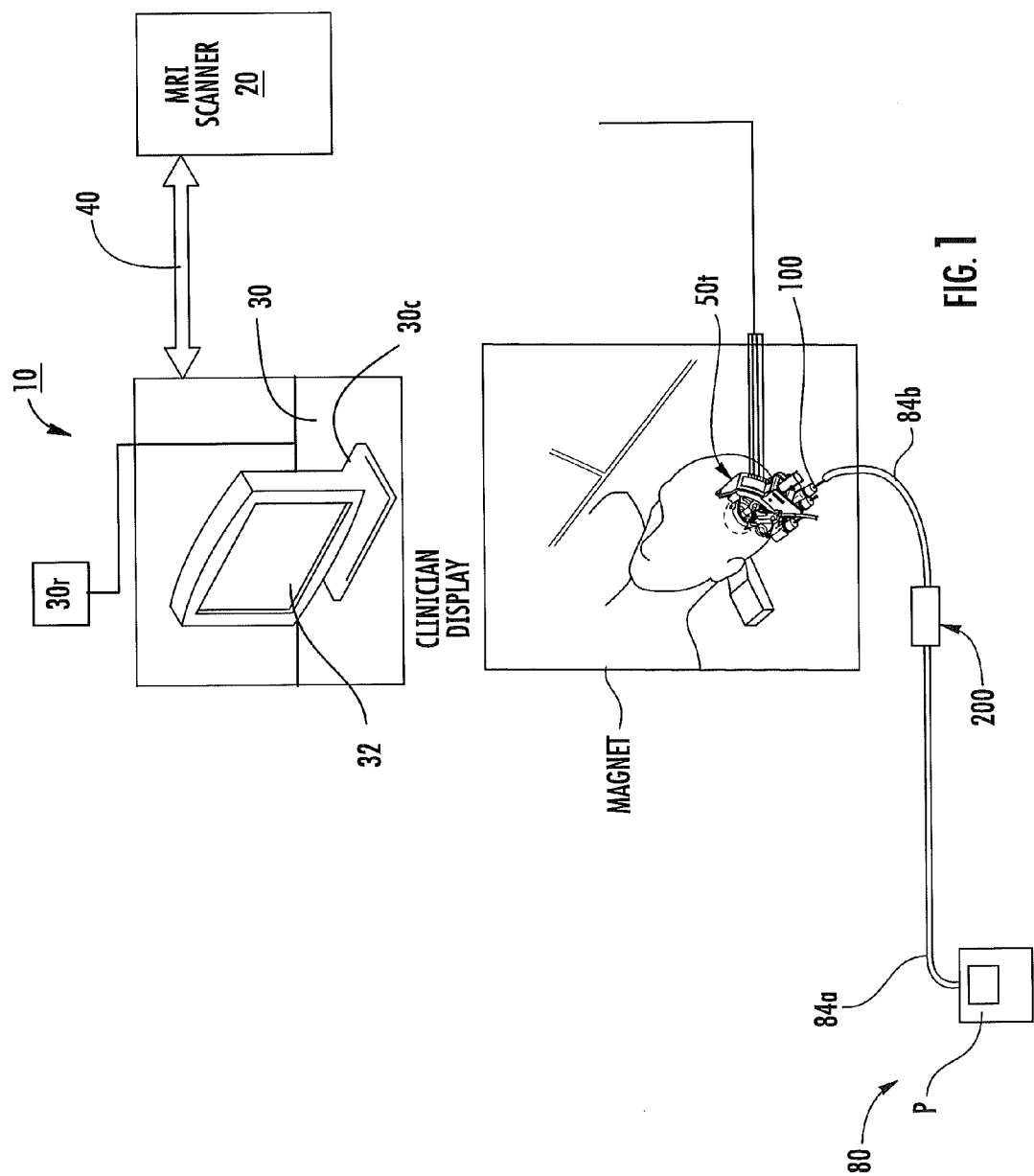
FIG. 1 is a schematic illustration of an MRI-guided interventional system in which embodiments of the present invention may be utilized.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/− twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "near real time" refers to both low latency and high frame rate. Latency is generally measured as the time from when an event occurs to display of the event (total processing time). For tracking, the frame rate can range from between about 100 fps to the imaging frame rate. In some embodiments, the tracking is updated at the imaging frame rate. For near 'real-time' imaging, the frame rate is typically between about 1 fps to about 20 fps, and in some embodiments, between about 3 fps to about 7 fps. The low latency required to be considered "near real time" is generally less than or equal to about 1 second. In some embodiments, the latency for tracking information is about 0.01 s, and typically between about 0.25-0.5 s when interleaved with imaging data. Thus, with respect to tracking, visualizations with the location, orientation and/or configuration of a known intrabody device can be updated with low latency between about 1 fps to about 100 fps. With respect to imaging, visualizations using near real time MR image data can be presented with a low latency, typically within between about 0.01 ms to less than about 1 second, and with a frame rate that is typically between about 1-20 fps. Together, the system can use the tracking signal and image signal data to dynamically present anatomy and one or more intrabody devices in the visualization in near real-time. In some embodiments, the tracking signal data is obtained and the associated spatial coordinates are determined while the MR image data is obtained and the resultant visualization(s) with the intrabody device (e.g., stylet) and the near RT MR image(s) are generated.

The terms "surgical cannula" and "cannula", as used herein, are interchangeable and refer to an intrabody cannula used to transfer a substance to a target intrabody location.

The term "sterile", as used herein, means that a device, kit, and/or packaging meets medical/surgical cleanliness guidelines, and typically is free from live bacteria or other microorganisms.

Embodiments of the present invention can be utilized with various diagnostic or interventional devices and/or therapies to any desired internal region of the body or object using MRI and/or in an MRI scanner or MRI interventional suite. The object can be any object, and may be particularly suitable for animal and/or human subjects. Some embodiments can be configured to deliver therapies that stimulate a desired region of the sympathetic nerve chain. Other uses inside or outside the brain include stem cell placement, gene therapy or drug delivery for treating physiological conditions, chemotherapy and drugs replicating therapy drugs. Some embodiments can be used to treat tumors.

The term "substance", as used herein, refers to a liquid for treating or facilitating diagnosis of a condition and can include bions, stem cells or other target cells to site-specific regions in the body, such as neurological target sites and the like. In some embodiments, stem cells and/or other cardio-rebuilding cells or products can be delivered into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6,539,263; 6,609,030 and 6,050,992, the contents of which are hereby incorporated by reference as if recited in full herein.

Embodiments of the present invention will now be described in further detail below with reference to the figures. FIG. 1 illustrates an MRI-guided interventional system 10 with an MRI scanner 20, a clinician workstation 30 with at least one circuit 30*c*, at least one display 32, an MRI compatible trajectory guide 50*t*, a depth stop 70 (FIG. 2), and a fluid substance delivery system 80. The fluid substance delivery system 80 includes an MRI-compatible intrabody surgical or delivery cannula 100, an infusion pump P, a substance delivery device 200, and connecting tubing 84*a*, 84*b*. The system 10 can be configured to render or generate real time visualizations of the target anatomical space using MRI image data and predefined data of at least one surgical tool to segment the image data and place the trajectory guide 50*t* and the cannula 100 in the rendered visualization in the correct orientation and position in 3D space, anatomically registered to a patient. The trajectory guide 50*t* and the cannula 100 can include or cooperate with tracking, monitoring and/or interventional components.

An exemplary trajectory guide 50*t* is illustrated in FIG. 1 in position on a patient. The trajectory guide 50*t* typically provides X-Y adjustment and pitch and roll adjustment in order to accurately position the cannula 100 at a desired location within a patient. For additional discussion of suitable trajectory guides, see U.S. Pat. No. 8,374,677, the contents of which are hereby incorporated by reference as if recited in full herein.

The tools of the system 10, including the cannula 100 and substance delivery device 200 (described below with respect to FIGS. 3-11) associated with the cannula 100, can be provided as a sterile kit (typically as single-use disposable hardware) or in other groups or sub-groups or even individually, typically provided in suitable sterile packaging.

Figure 2:
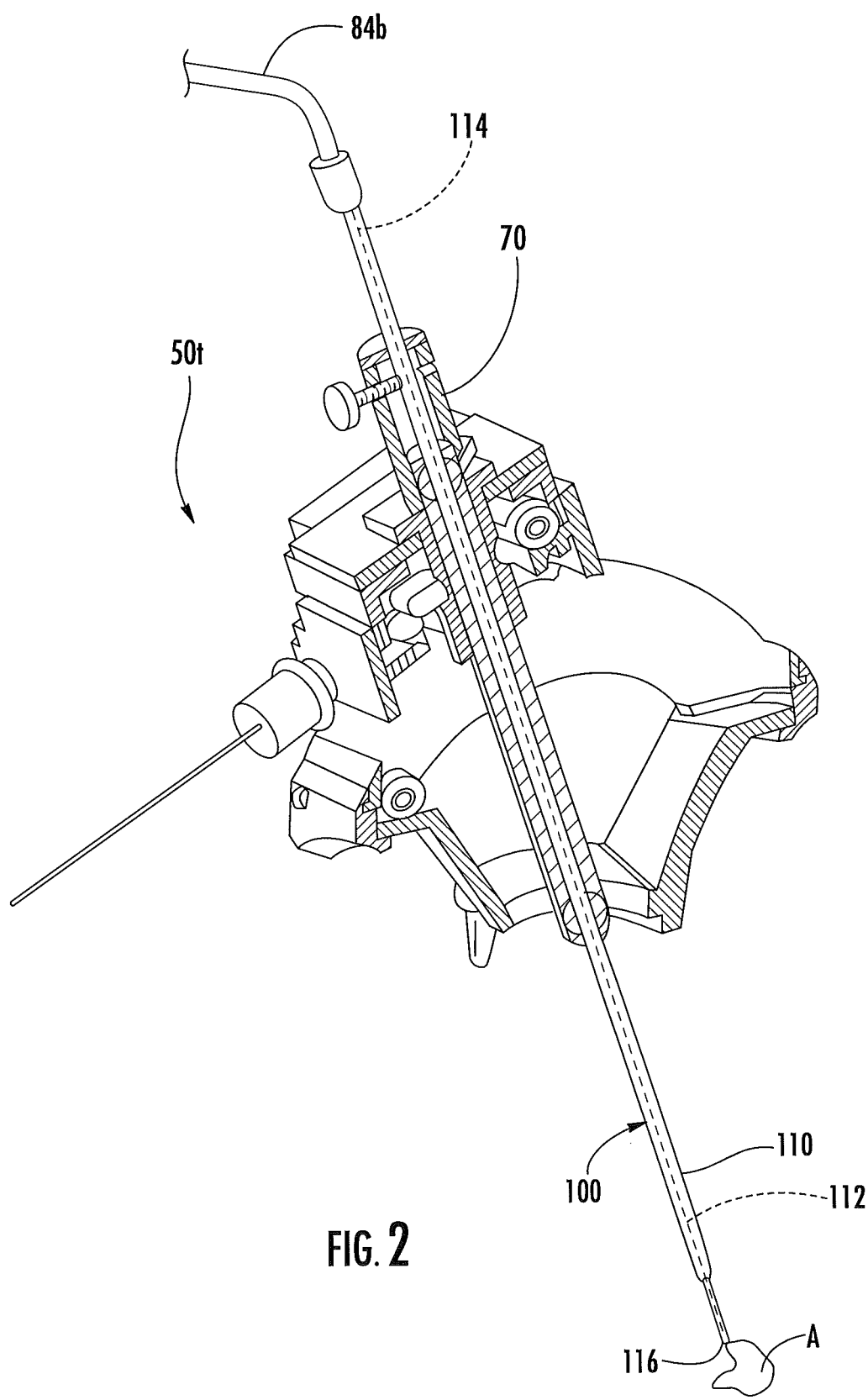
FIG. 2 is a sectional view of the trajectory guide of the MRI-guided system of FIG. 1 with a surgical cannula for transferring a substance (e.g., an infusate, etc.) to a patient.

The cannula 100 can be configured to flowably introduce and/or inject a desired therapy substance (e.g., antigen, gene therapy, chemotherapy or stem-cell or other therapy type). The cannula 100 as shown in FIG. 2, is an exemplary cannula and various other types of cannulas can be utilized with a substance delivery device 200, according to embodiments of the present invention. The illustrated cannula 100 includes a cannula body 110 defining at least one longitudinally extending lumen 112, an inlet port 114 and at least one exit port 116. The cannula 100 typically is formed of an MRI-compatible, MRI-visible material such as ceramic. For additional discussion of exemplary cannulas that can be used with embodiments of the present invention, see U.S. Patent Application Publication No. US 2013/0030408, the contents of which are hereby incorporated by reference as if recited in full herein.

The lumen 112 is fluidly connected to the substance delivery device 200 via tubing 84*b* (FIGS. 1, 2, 10 and 11), and the substance delivery device 200 is fluidly connected to the pump P via tubing 84*a* (FIGS. 1, 2, 10 and 11). The tubing 84*a*, 84*b* may be flexible tubing. According to some embodiments, the tubing 84*a*, 84*b* is PVC tubing. According to some embodiments, the tubing 84*a*, 84*b* is silicone tubing. The tubing 84*a*, 84*b* may have various lengths. For example, in some embodiments, the tubing may be six to ten feet (6 ft-10 ft) in length, although other lengths are possible. Typically, tubing 84*b* is considerably shorter than tubing 84*a* in order to reduce the distance the substance A has to travel to the cannula 100 and thereby reduce volume thereof that is wasted. For example, the tubing 84b may be only a few inches in length in some embodiments. In other embodiments, the tubing 84b is eliminated altogether and the substance delivery device is connected directly to the rigid part of an infusion cannula (or a catheter or biopsy needle, etc.).

As will be described further below with respect to FIG. 11, the pump P is configured to move the push rod 250r of a syringe 250 containing a slave fluid F such that the slave fluid is forced out of the syringe 250. The resulting pressure of the slave fluid F causes the diaphragm 210 within the substance delivery device 200 to move which, in turn forces the substance A out of the substance delivery device 200, through the tubing 84b (if provided) and into the cannula 100.

The substance (A, FIG. 2) delivered to the target region through the delivery cannula 100 may be any suitable and desired substance. According to some embodiments, the substance A is a liquid or slurry. In the case of a tumor, the substance A may be a chemotherapeutic (cytotoxic) fluid. In some embodiments, the substance A can include certain types of advantageous cells that act as vaccines or other medicaments (for example, antigen presenting cells such as dentritic cells). The dentritic cells may be pulsed with one or more antigens and/or with RNA encoding one or more antigen. Exemplary antigens are tumor-specific or pathogen-specific antigens. Examples of tumor-specific antigens include, but are not limited to, antigens from tumors such as renal cell tumors, melanoma, leukemia, myeloma, breast cancer, prostate cancer, ovarian cancer, lung cancer and bladder cancer. Examples of pathogen-specific antigens include, but are not limited to, antigens specific for HIV or HCV. In some embodiments, the substance A may comprise radioactive material such as radioactive seeds. Substances A delivered to a target area in accordance with embodiments of the present invention may include, but are not limited to, the following drugs (including any combinations thereof) listed in Table 1. Exemplary disorders that can be treated by the various drugs are also listed in Table 1.

TABLE 1

| DRUG (generic name) | DISORDER(S) |
| --- | --- |
| Caprylidene | Alzheimer's disease |
| Donepezil | Alzheimer's disease |
| Galantamine | Alzheimer's disease |
| Memantine | Alzheimer's disease |
| Tacrine | Alzheimer's disease |
| vitamin E | Alzheimer's disease |
| ergoloid mesylates | Alzheimer's disease |
| Riluzole | Amyotrophic lateral sclerosis |
| Metoprolol | Benign essential tremors |
| Primidone | Benign essential tremors |
| Propanolol | Benign essential tremors |
| Gabapentin | Benign essential tremors & Epilepsy |
| Nadolol | Benign essential tremors & Parkinson's disease |
| Zonisamide | Benign essential tremors & Parkinson's disease |
| Carmustine | Brain tumor |
| Lomustine | Brain tumor |
| Methotrexate | Brain tumor |
| Cisplatin | Brain tumor & Neuroblastoma |
| Ioversol | Cerebral arteriography |
| Mannitol | Cerebral Edema |
| Dexamethasone | Cerebral Edema & Neurosarcoidosis |
| Baclofen | Cerebral spasticity |
| Ticlopidine | Cerebral thrombosis/embolism |
| Isoxsuprine | Cerebrovascular insufficiency |
| Cefotaxime | CNS infection & Meningitis |
| Acyclovir | Encephalitis |
| Foscarnet | Encephalitis |
| Ganciclovir | Encephalitis |
| interferon alpha-2a | Encephalitis |
| Carbamazepine | Epilepsy |
| Clonazepam | Epilepsy |
| Diazepam | Epilepsy |
| divalproex sodium | Epilepsy |
| Ethosuximide | Epilepsy |
| Ethotoin | Epilepsy |
| Felbamate | Epilepsy |
| Fosphenytoin | Epilepsy |
| Levetiracetam | Epilepsy |
| Mephobarbital | Epilepsy |
| Paramethadione | Epilepsy |
| Phenytoin | Epilepsy |
| Trimethadione | Epilepsy |
| Pregabalin | Epilepsy & Neuralgia |
| immune globulin intravenous | Guillain-Barre Syndrome |
| interferon beta-1b | Guillain-Barre Syndrome & Multiple sclerosis |
| Azathioprine | Guillain-Barre Syndrome & Multiple sclerosis & Neurosarcoidosis |
| Risperidone | Head injury |
| Tetrabenazine | Huntington's disease |
| Acetazolamide | Hydrocephalus & Epilepsy |
| Alteplase | Ischemic stroke |
| Clopidogrel | Ischemic stroke |

TABLE 1-continued

| DRUG (generic name) | DISORDER(S) |
| --- | --- |
| Nimodipine | Ischemic stroke & Subarachnoid hemorrhage |
| Aspirin | Ischemic stroke & Thromboembolic stroke |
| Amikacin | Encaphalitis |
| Ampicillin | Encaphalitis |
| ampicillin/sulbactam | Encaphalitis |
| Ceftazidime | Encaphalitis |
| Ceftizoxime | Encaphalitis |
| Cefuroxime | Encaphalitis |
| Chloramphenicol | Encaphalitis |
| cilastatin/imipenem | Encaphalitis |
| Gentamicin | Encaphalitis |
| Meropenem | Encaphalitis |
| Metronidazole | Encaphalitis |
| Nafcillin | Encaphalitis |
| Oxacillin | Encaphalitis |
| Piperacillin | Encaphalitis |
| Rifampin | Encaphalitis |
| sulfamethoxazole/trimethoprim | Encaphalitis |
| Tobramycin | Encaphalitis |
| Triamcinolone | Encaphalitis |
| Vancomycin | Encaphalitis |
| Ceftriaxone | Encaphalitis & Neurosyphilis |
| Penicillin | Encaphalitis & Neurosyphilis |
| Corticotrophin | Multiple sclerosis |
| Dalfampridine | Multiple sclerosis |
| Glatiramer | Multiple sclerosis |
| Mitoxantrone | Multiple sclerosis |
| Natalizumab | Multiple sclerosis |
| Modafinil | Multiple sclerosis |
| Cyclophosphamide | Multiple sclerosis & Brain tumor & Neuroblastoma |
| interferon beta-1a | Multiple sclerosis & Neuritis |
| Prednisolone | Multiple sclerosis & Neurosarcoidosis |
| Prednisone | Multiple sclerosis & Neurosarcoidosis |
| Amantadine | Multiple sclerosis & Parkinson's disease |
| Methylprednisolone | Neuralgia |
| Desvenlafaxine | Neuralgia |
| Nortriptyline | Neuralgia |
| Doxorubicin | Neuroblastoma |
| Vincristine | Neuroblastoma |
| Albendazole | Neurocystecercosis |
| chloroquine phosphate | Neurosarcoidosis |
| Hydroxychloroquine | Neurosarcoidosis |
| Infliximab | Neurosarcoidosis |
| Pentoxyfilline | Neurosarcoidosis |
| Thalidomide | Neurosarcoidosis |
| Apomorphine | Parkinson's disease |
| Belladonna | Parkinson's disease |
| Benztropine | Parkinson's disease |
| Biperiden | Parkinson's disease |
| Bromocriptine | Parkinson's disease |
| Carbidopa | Parkinson's disease |
| carbidopa/entacapone/levodopa | Parkinson's disease |
| carbidopa/levodopa | Parkinson's disease |
| Entacapone | Parkinson's disease |
| Levodopa | Parkinson's disease |
| pergolide mesylate | Parkinson's disease |
| Pramipexole | Parkinson's disease |
| Procyclidine | Parkinson's disease |
| Rasagiline | Parkinson's disease |
| Ropinirole | Parkinson's disease |
| Rotiotine | Parkinson's disease |
| Scopolamine | Parkinson's disease |
| Tolcapone | Parkinson's disease |
| Trihexyphenidyl | Parkinson's disease |
| Seleginline | Parkinson's disease |
| Rivastigmine | Parkinson's disease & Alzheimer's disease |
| Anisindione | Thromboembolic stroke |
| Warfarin | Thromboembolic stroke |
| 5-hydroxytryptophan | Depression & Anxiety & ADHD |
| Duloxetine | Depression & Anxiety & Bipolar disorder |
| Escitalopram | Depression & Anxiety & Bipolar disorder |
| Venlafaxine | Depression & Anxiety & Bipolar disorder & Autism & Social anxiety disorder |
| Desvenlafaxine | Depression & Anxiety & PTSD & ADHD |
| Paroxetine | Depression & Anxiety & PTSD & Social anxiety disorder |
| fluoxetine/olanzapine | Depression & Bipolar disorder |
| 1-methylfolate | Depression & BPD |

TABLE 1-continued

| DRUG (generic name) | DISORDER(S) |
| --- | --- |
| Amitriptyline | Depression & PTSD |
| Sertraline | Depression & PTSD & Bipolar disorder & Social anxiety disorder |
| Fluvoxamine | Depression & PTSD & Social anxiety disorder |
| Olanzapine | Depression & Schizophrenia & Bipolar disorder |
| Paliperidone | Depression & Schizophrenia & Bipolar disorder |
| Aripiprazole | Depression & Schizophrenia & Bipolar disorder & Autism |
| Quetiapine | Depression & Schizophrenia & PTSD & BPD & Bipolar disorder |
| Risperidone | Depression & Schizophrenia & PTSD & BPD & Bipolar disorder & Autism |
| Amisulpride | Depression & Social anxiety disorder |
| Chlorpromazine | Psychosis |
| Droperidol | Psychosis |
| Fluphenazine | Psychosis |
| Periciazine | Psychosis |
| Perphenazine | Psychosis |
| Thiothixene | Psychosis |
| Triflupromazine | Psychosis |
| Haloperidol | Psychosis & Dementia |
| Prazosin | PTSD |
| Clozapine | Schizophrenia |
| Flupenthixol | Schizophrenia |
| Iloperidone | Schizophrenia |
| Loxapine | Schizophrenia |
| Mesoridazine | Schizophrenia |
| Promazine | Schizophrenia |
| Reserpine | Schizophrenia |
| Thioridazein | Schizophrenia |
| Zuclopenthixol | Schizophrenia |
| Asenapine | Schizophrenia & Bipolar disorder |
| Levomepromazine | Schizophrenia & Bipolar disorder |
| Ziprasidone | Schizophrenia & Bipolar disorder |
| Molindone | Schizophrenia & Psychosis |
| Pimozide | Schizophrenia & Psychosis |
| Thioridazine | Schizophrenia & Psychosis |
| Cytarabine | Chemotherapy, hematological malignancies |

Referring now to FIG. 3, a substance delivery device 200 for use with the fluid substance delivery system 80 of FIGS. 1-2 is illustrated. The substance delivery device 200 includes a tubular body 202 having a hollow interior 202i, and opposing proximal and distal ends 204, 206. The tubular body 202 may be formed from various materials including, but not limited to, glass and polymeric material, and may be formed from MRI-compatible material. A diaphragm 210 is in slideable sealing engagement with an inside wall 202w of the tubular body 202. The diaphragm 210 is movable back and forth within the tubular body 202 between the proximal and distal ends 204, 206. In some embodiments, the diaphragm 210 is formed from an elastomeric material. In some embodiments, the diaphragm 210 is formed from a substantially rigid polymeric material.

The tubular body 202 may be sized to receive different volumes of a substance A and/or slave fluid F. Substance delivery devices 200 that are utilized with embodiments of the present invention can have various sizes. For example, substance delivery devices 200 may be sized to hold less than twenty microliters (20 µL) of a substance A. Other substance delivery devices 200 may be sized to hold twenty microliters (20 µL) or more of a substance A. An exemplary range of substance volumes within a substance delivery device 200 is between about twenty microliters (20 µL) and about thirty milliliters (30 cc), between about twenty five microliters (25 µL) and about thirty milliliters (30 cc), between about thirty microliters (30 µL) and about thirty milliliters (30 cc), between about thirty five microliters (35 µL) and about thirty milliliters (30 cc), between about forty microliters (40 µL) and about thirty milliliters (30 cc), between about forty five microliters (45 µL) and about thirty milliliters (30 cc), between about fifty microliters (50 µL) and about thirty milliliters (30 cc); however, other ranges are possible.

Referring to FIG. 4, a typically biocompatible slave fluid F, such as a saline solution, etc., is being loaded into the substance delivery device 200 via a syringe 250 in fluid communication with the tubular body proximal end 204. The volume of the slave fluid F loaded within the tubular body 202 can vary depending on the volume of the substance A to be loaded in the tubular body 202 on the opposite side of the diaphragm 210, as well as on the size of the substance delivery device 200. The slave fluid F can be virtually any type of fluid and typically is a fluid, such as saline, that is not harmful if injected into a patient.

Figure 5B:
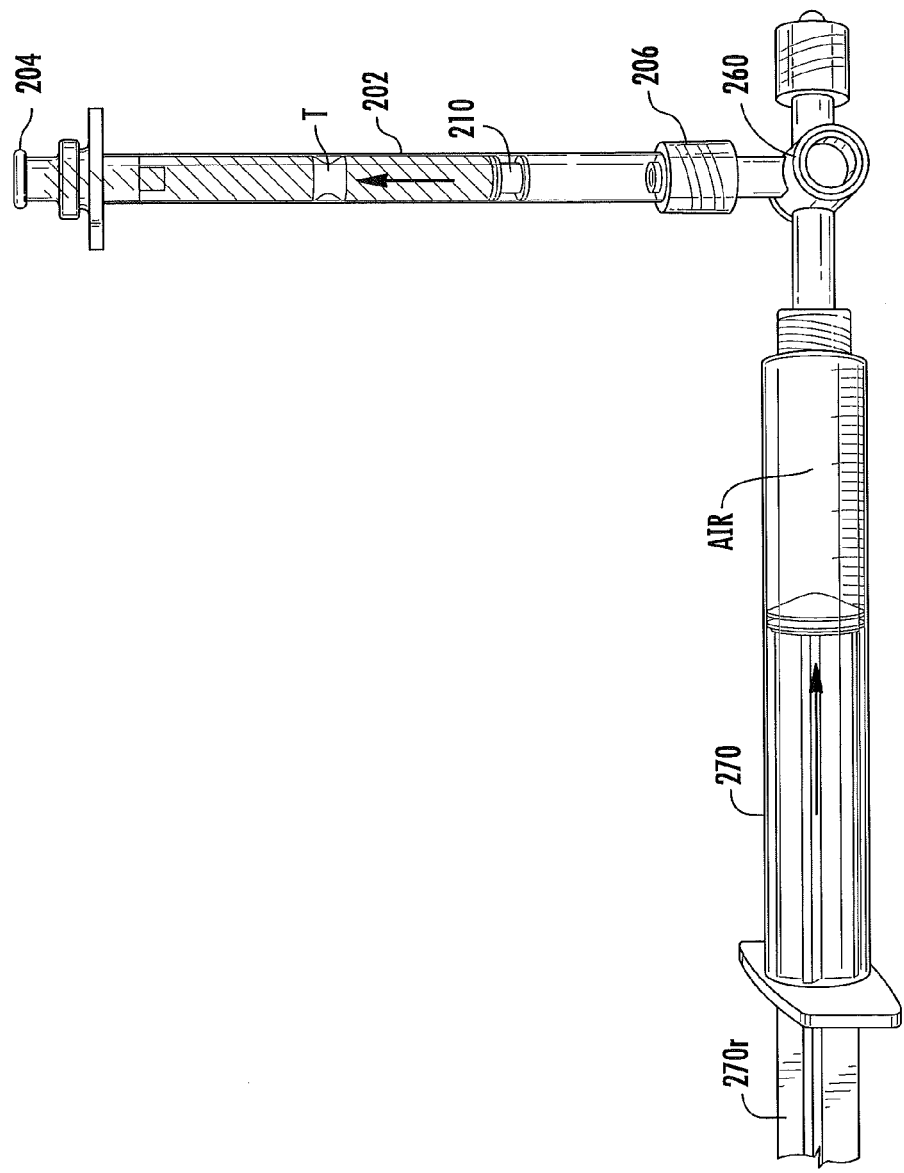
Figure 5A:
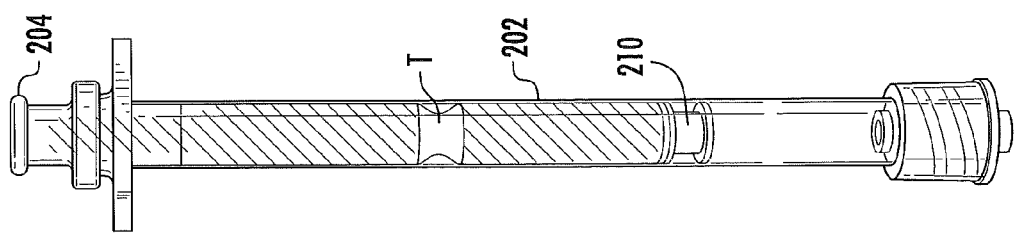

In FIGS. 5A-5B, the syringe 250 illustrated in FIG. 4 has been removed from the tubular body proximal end 204 and air T trapped in the slave fluid is being removed. For example, in FIG. 5B, a stopcock 260 is connected to the tubular body distal end 206 and a syringe 270 containing air (or another gas) is connected to the stopcock 260. User activation of the plunger rod 270r of the syringe 270 forces air into the distal end 206 of the tubular body 202 which, in turn, moves the diaphragm 210 upwards, as illustrated. This upward movement of the diaphragm 210 forces the slave fluid F upwardly such that trapped air T can be expelled through the tubular body proximal end 204, as would be understood by one skilled in the art. FIG. 5C illustrates the tubular body 202 loaded with slave fluid F and with all trapped air removed therefrom.

Referring now to FIG. 6, tubing 84a is connected to the syringe 250 containing the slave fluid F, and the tubing 84a is being filled with the slave fluid F from the syringe 250. When the tubing 84a is completely filled with the slave fluid F and all trapped air is removed therefrom, the tubing 84a is connected to the substance delivery device 200 that has been loaded with the slave fluid F. As illustrated in FIG. 7, the tubing 84a is connected to the tubular body proximal end 204 via connector 85f, such as a Luer lock connector. The connector 85f matingly engages with a connector 204f at the tubular body proximal end 204. Activation of the plunger rod 250r of syringe 250 in the direction of arrow A1 thereby causes the slave fluid to force the diaphragm 210 in the substance delivery device 200 in the direction of arrow A2 (i.e., towards the tubular body distal end 206). Similarly, activation of the plunger rod 250r of syringe 250 in the direction of arrow A3 thereby causes the slave fluid to force the diaphragm 210 in the substance delivery device 200 in the direction of arrow A4 (i.e., towards the tubular body proximal end 206).

Figure 8A:
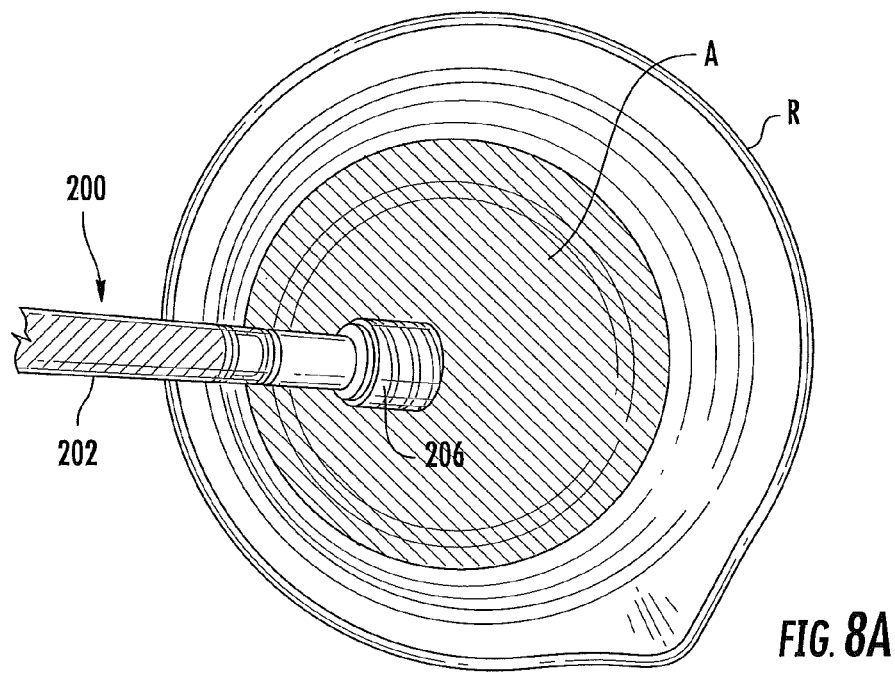
FIGS. 8A-8B illustrate loading a substance through the distal end of the substance delivery device tubular body of FIG. 3 by pulling the diaphragm in the tubular body towards the tubular body proximal end via the slave fluid.
Figure 8B:
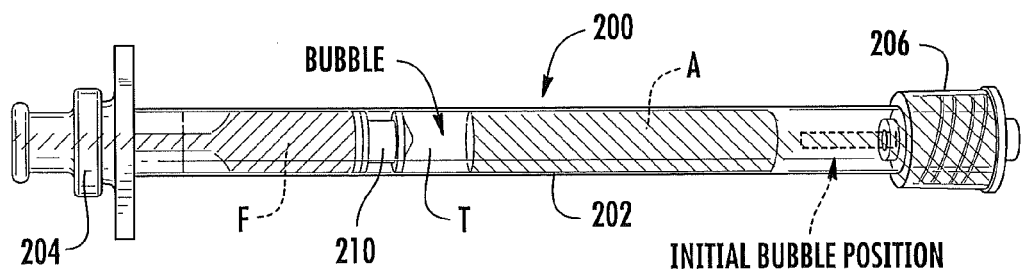

Referring now to FIGS. 8A-8B, the substance delivery device 200 of FIG. 7 is being loaded with a substance A. In FIG. 8A, the distal end 206 of the tubular body 202 is lowered within a reservoir R of the substance A. The reservoir R can be enclosed for a sterile environment and/or flexible packaging. By pulling on the plunger rod 250r of the syringe 250 in the direction of A3 (FIG. 7), the slave fluid F and diaphragm 210 move in the direction indicated by arrow A4 and the substance A is drawn into the tubular body 202 through the distal end 206 thereof. FIG. 8B illustrates air T trapped in the substance delivery device 200 between the slave fluid F and the substance A.

Figure 9A:
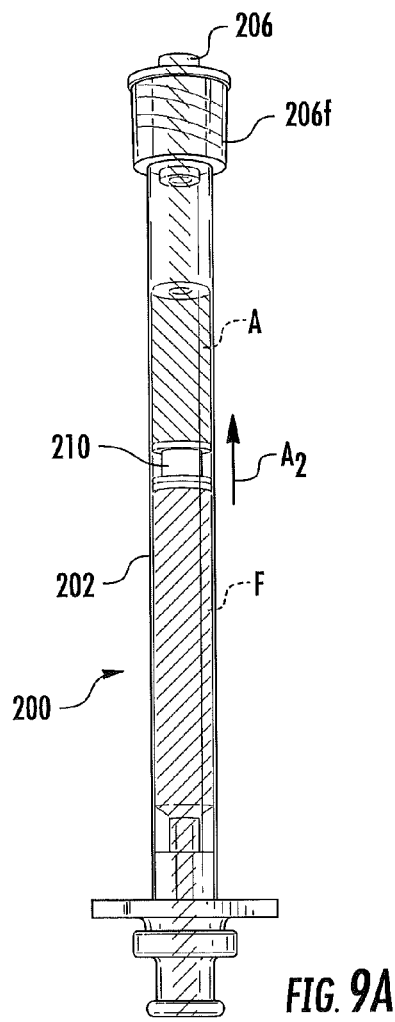
FIG. 9A illustrates removing trapped air from the substance in the substance delivery device of FIGS. 8A-8B.
Figure 9B:
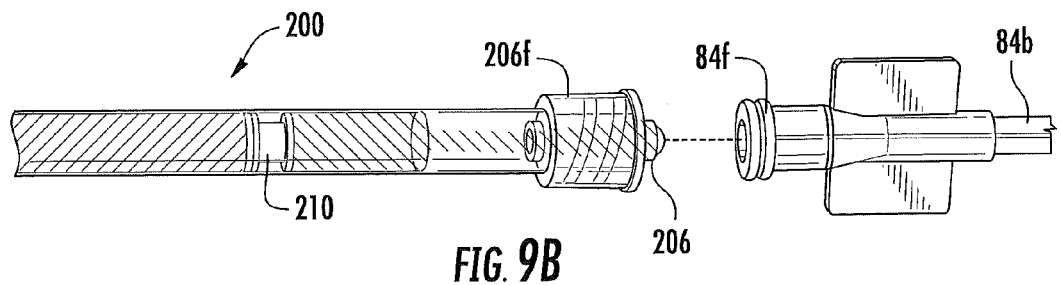
FIG. 9B is a partial view of the substance delivery device of FIG. 9A and illustrating tubing that can be secured to the distal end of the substance delivery device.

As illustrated in FIG. 9A, air trapped in the substance A is removed from the tubular body 202 by pushing the diaphragm 210 upwardly in the direction of arrow A2 via the slave fluid A. As illustrated in FIG. 9B, tubing 84b is adapted to be secured to the tubular body distal end 206 via a fitting 84f that matingly engages a connector 206f at the distal end 206. For example, the fitting 84f may be a threaded connector, such as a Luer lock connector, that threadingly engages corresponding threads on the connector 206f. Once the substance delivery device 200 of FIG. 9B is connected to the tubing 84b, the substance A can be forced, via the slave fluid F, through the tubing 84b and into a cannula 100 (FIG. 10) for injection into a patient.

All or some of the various preparatory operations described above can be carried out on site or can be performed remotely and a drug delivery device 200 filled with a slave fluid and/or substance A can be provided as a sterile package ready for use and with a defined shelf life.

Figure 10:
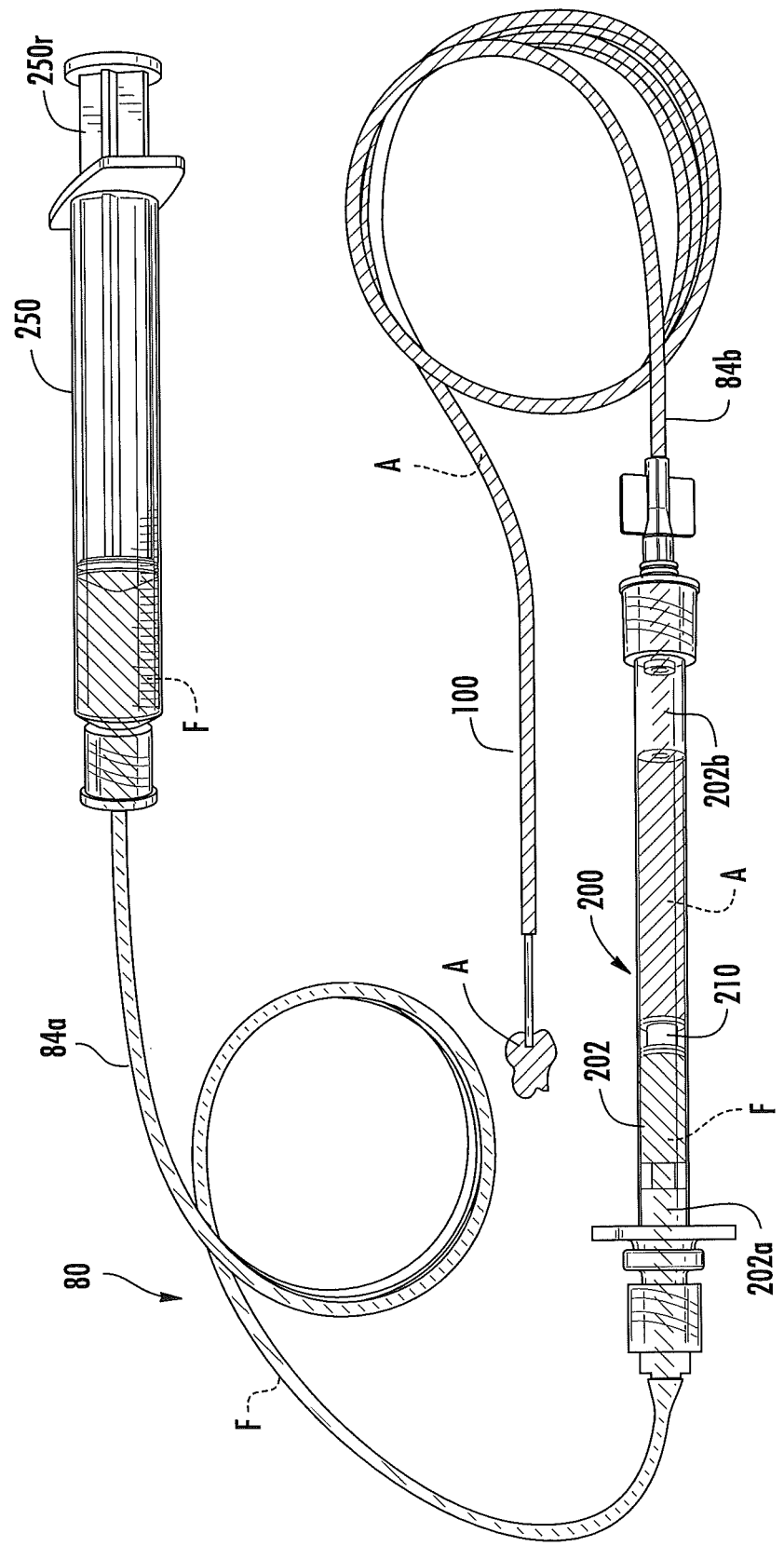
FIG. 10 illustrates a fluid substance delivery system, according to some embodiments of the present invention.

In FIG. 10, the drug delivery system 80 is complete and ready for delivering the substance A to a patient. Forcing the slave fluid F out of the syringe 250 by pressing the plunger rod 250r causes the diaphragm 210 in the substance delivery device 200 to force the substance A out of the substance delivery device 200, through the tubing 84b (if utilized), and through the cannula 100.

Figure 11:
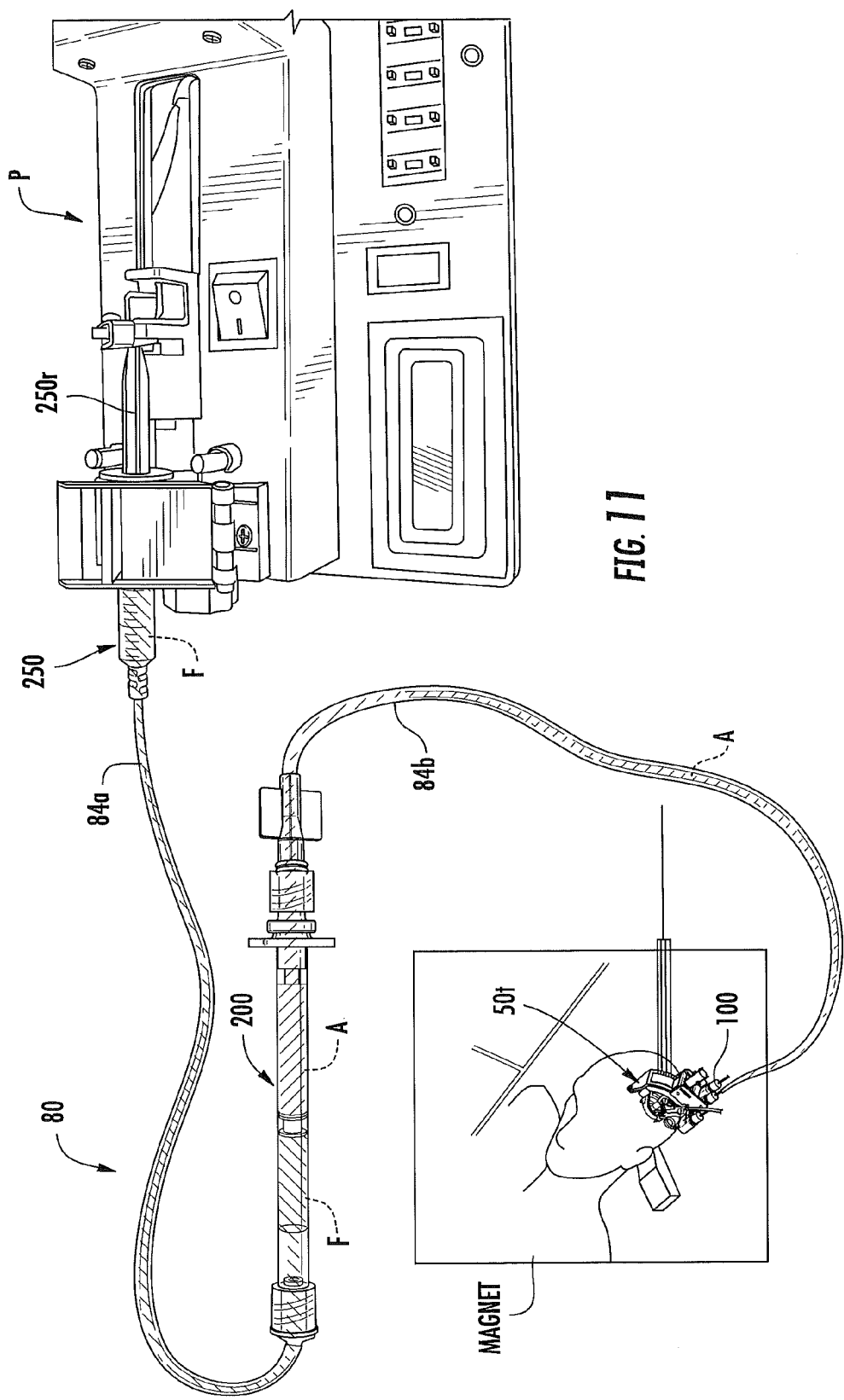
FIG. 11 illustrates a fluid substance delivery system, according to some embodiments of the present invention.

In FIG. 11, the syringe 250 is mounted to a pump P that is configured to push the syringe plunger rod 250r. When the plunger rod 250r is pushed by the pump P, the slave fluid F causes the diaphragm 210 in the substance delivery device 200 between the slave fluid F and the substance A to force the substance A to flow downstream through the tubing 84b (if utilized) and into the cannula 100. In some embodiments, the tubing 84b may be only a few inches in length. In other embodiments, the tubing 84b is eliminated altogether and the substance delivery device is connected directly to the cannula 100 (or another device, such as a catheter, biopsy needle, etc.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A system for delivering a substance to a patient, the system comprising:
    a trajectory guide configured to be secured to a body of the patient;
    a cannula supported by the trajectory guide, the cannula comprising a cannula body defining at least one longitudinally extending lumen, an inlet port, and at least one exit port, wherein the trajectory guide provides X-Y adjustment and pitch and roll adjustment for the cannula;
    a substance delivery device, comprising:
        an elongated tubular body comprising opposing proximal and distal ends, each of the proximal and distal ends comprising a respective connector;
        a diaphragm that is in slideable sealing engagement with an inside wall of the tubular body, wherein the diaphragm is movable in opposite first and second directions within the tubular body; and
        a slave fluid contained within the tubular body between the diaphragm and the tubular body proximal end; and
    a syringe in fluid communication with the tubular body proximal end via first flexible tubing having a connector that is matingly and removably secured to the tubular body proximal end connector, wherein the syringe and the first flexible tubing contain the slave fluid, wherein activation of the syringe to cause the slave fluid to move the diaphragm in the second direction causes a substance to be loaded within the tubular body between the diaphragm and the tubular body distal end;
    wherein the at least one longitudinally extending lumen of the cannula is fluidly connected to the tubular body distal end via second flexible tubing, and wherein the cannula is adapted to transfer the substance from the tubular body to a selected location in the patient via the at least one exit port upon activation of the syringe to cause the slave fluid to move the diaphragm in the first direction.

2. The system of claim 1, wherein the second tubing comprises a connector that is matingly and removably connected to the tubular body distal end connector.

3. The system of claim 1, wherein the cannula is MRI-compatible.

4. The system of claim 1, wherein the substance delivery device is formed of MRI-compatible material.

5. The system of claim 1, further comprising a pump adapted to move a plunger in the syringe and cause the slave fluid to move the diaphragm in the first and second directions.

6. The system of claim 1, wherein a volume of the substance is less than twenty microliters (20 µL).

7. The system of claim 1, wherein a volume of the substance is between about twenty microliters (20 μL) and about thirty milliliters (30 cc).

8. The system of claim 1, wherein the substance is a liquid medicament.

9. The system of claim 8, wherein the liquid medicament is a brain therapy medicament.

10. The system of claim 1, wherein an exterior surface of the cannula has at least first and second co-axially disposed segments having different outer diameters.

11. The system of claim 10, wherein the exterior surface includes a tapered transition between the first and second segments.

12. The system of claim 1, wherein the first flexible tubing has a first length, and wherein the second flexible tubing has a second length that is substantially less than the first length.

13. The system of claim 12, wherein the first length is at least about six feet (6 ft).

* * * * *